United States Patent [19]

Mellows

[11] 3,956,630
[45] May 11, 1976

[54] FLUORIMETRIC COAT WEIGHT MEASUREMENT

[75] Inventor: Frank W. Mellows, Columbia, Md.

[73] Assignee: Westvaco Corporation, New York, N.Y.

[22] Filed: Mar. 14, 1975

[21] Appl. No.: 558,446

[52] U.S. Cl. .............................. 250/302; 250/252; 250/461 R
[51] Int. Cl.² ......................................... G09K 3/00
[58] Field of Search ............ 250/252, 302, 458, 461

[56] References Cited
UNITED STATES PATENTS

| | | | |
|---|---|---|---|
| 3,334,230 | 8/1967 | Shaffer | 250/252 |
| 3,675,015 | 7/1972 | Geib | 250/302 |

*Primary Examiner*—Davis L. Willis

[57] ABSTRACT

A method and apparatus is disclosed for the on-machine measurement of coat weights of coatings applied to paper webs or the like. The invention provides an accuracy of plus or minus 0.1 pound per ream of coating in the coat weight range of from about 0 to 5 pounds per ream. Higher coat weights can be measured by practicing the method of the present invention, however the accuracy of the measurements of higher coat weights is reduced with an upper limit in the range of from about 10 to 20 pounds per ream depending upon the coating formulation being applied. The invention permits separate coat weight measurements of a web coated both sides and is carried out by including a small amount of a fluorescing optical brightener in the coating applied. The level of fluorescence of the optical brightener is continuously measured under a UV light source and the readings obtained are converted to determine the coat weight applied.

9 Claims, 6 Drawing Figures

FLUORIMETRIC COAT WEIGHT MEASUREMENT

BACKGROUND OF INVENTION

The present invention provides an accurate technique for continuously making on-machine measurements, on selected off-machine measurements of low coat weights applied to paper in the range where conventional methods such as the beta gauge technique or the coating consumption technique have proven to be inaccurate and unreliable. The beta gauge technique is fully described in U.S. Pat. Nos. 3,019,336 and 3,130,303, however, the percentage of error of coat weights in the range of from about 0 to 5 pounds per ream has been found to be large with the beta gauge method. Coat weights as measured by the coating consumption technique are reasonably accurate, but the results obtained only yield an average coat weight over a given period of time with no indication of coat weight variation on the web in either the cross direction or machine direction of the web. Of course there are other known methods of measuring coat weights applied to a paper web or the like, but they are generally off-machine methods employing a chemical analysis or ash determination.

For the purpose of the present invention a ream of paper is defined as 3300 square feet of paper, or 500 sheets measuring 25 × 38 inches.

SUMMARY OF INVENTION

The invention herein relates to a novel method for measuring the coat weight applied to paper or the like. More specifically, the invention relates to a method and apparatus for continuously monitoring and accurately measuring low coat weight coatings as applied to paper in a paper making operation. In addition, the method and apparatus disclosed is also useful for making selected off-machine coat weight measurements.

In accordance with the general principles of the present invention, a fluorescing optical brightener is added to a coating formulation and the level of fluorescence of the applied coating is continuously and quantitatively measured by exposure to UV light. Simultaneously, the amount of coating applied is also determined by an independent off machine process such as a chemical analysis or ash determination, and the fluorescent readings are related to the coat weights as measured by the independent method to obtain a plot of fluorescence vs. coat weight over the coat weight range desired. The object, of course, is to obtain a linear plot for the particular coating formulation over the coat weight range desired for maximum accuracy. After this step is performed, the fluorescence reading device can then be calibrated directly with coat weight numbers or the plot can be kept at hand for reference as needed. A reference plot is required for each coating formulation, and in each case, the type of optical brightener selected, the amount of optical brightener added to the coating and the sensitivity of the UV light system used all play a role in obtaining the most accurate plot over the desired coat weight range. However, after the fluorescence data for a given coating formulation is obtained, fluorescence readings taken in the cross direction and machine direction of the web give an accurate indication of the coating lay on the web. Moreover, unlike the beta gauge technique which relies on a differential measurement of the web before and after the coating is applied to determine the coat weight, the fluorimetric method of the present invention relies on a surface measurement only of the coating applied. Thus the readings obtained with the fluorimetric method are not affected by the substrate on which the coating is applied, and because of this fact, coatings having a coat weight of, for instance, less than 1 pound per ream, can be measured using the fluorimetric method of the present invention as accurately (on a percentage basis) as coat weights of 3–4 pounds per ream. Furthermore, since only a surface measurement is involved with the fluorimetric method disclosed, separate coat weights may be measured simultaneously on each side of a coated two side (C2S) web.

DETAILED DESCRIPTION

A coat weight measuring method and apparatus is disclosed that allows on-machine coat weight measurements of coatings applied to a paper web or the like in the coat weight range of from about 0 to 5 pounds per ream with excellent sensitivity. Changes in coat weight in the range specified of plus or minus 0.1 pounds per ream can be detected with great precision. Higher coat weights can also be measured by practicing the method of the present invention, however the accuracy of the measurements of higher coat weights is reduced with an upper limit in the range of from about 10 to 20 pounds per ream depending upon the coating formulation applied.

The method of the present invention involves the addition of a low concentration of a fluorescing optical brightener to the coating to be applied, which concentration is less than that normally used to improve sheet brightness. The coat weight measurement is then carried out by measuring the fluroesence of the applied coating with an optical device substantially as shown schematically in FIG. 1.

Figure 1:
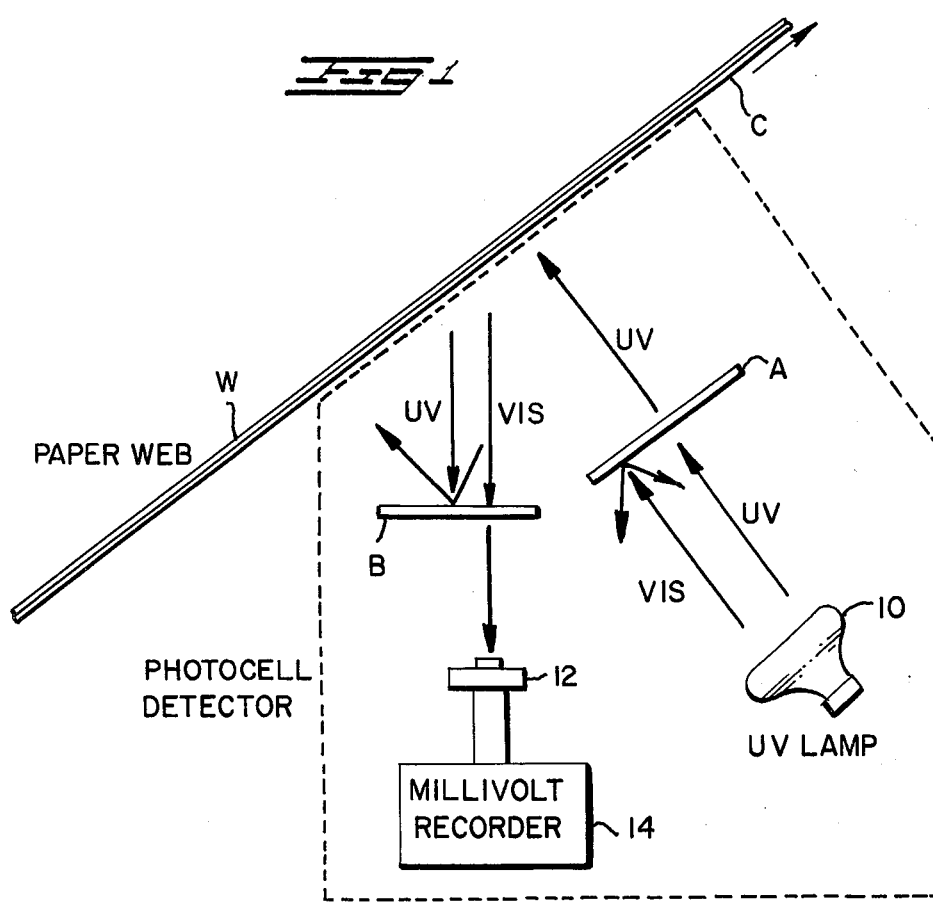
FIG. 1 is a schematic illustration of typical apparatus that could be used with the fluorimetric coat weight measurement method disclosed.

The illustration in FIG. 1 is intended to demonstrate the basic principles of the coat weight measurement apparatus of the present invention. The coating C on web W is applied with any known web coating device and either before or after the web is dried, the coated side of the web W is scanned to obtain the desired coat weight measurements. The coat weight measurement method of the present invention involves the use of a UV light source, optical filters, a photocell detector, a recording device and a fluorescing optical brightener in the coating. The mechanism of the present invention relies on the principle of fluorescence which may be defined as the production of visible light by a substance as the result of exposure to and absorption of other radiation of a shorter wave length (such as ultraviolet light). The preferred optical brightener is a fluorescent compound which absorbs ultraviolet light and emits it as visible light usually in the blue region of the spectrum of from about 400-500 nanometers.

As shown in FIG. 1, a UV light source 10 is directed toward the coated side of the web identified as C. The UV lamp emits both ultraviolet radiation and visible radiation, however a filter A, of the visible absorbing UV transmitting type, is positioned between the UV light source 10 and the coated side of the web C. Filter A permits only UV light to pass which light is then absorbed by the optical brightener in the coating applied to the web. The absorbed UV light is converted to visible radiation which is then filtered through a second filter B of the UV absorbing and visible transmitting type. Thus the only light which passes through the filter B consists of visible light which is then interrupted by the photocell detector 12 and the amount of visible light intercepted is recorded on the recording device 14 which can be calibrated to yield coat weight measurements.

In one embodiment of the present invention both the UV lamp 10 and the photocell detector 12 are mounted in an enclosure having the approximate dimensions 10×8×6 inches (length × width × depth) to form a unit that can be used to scan the travelling coated web. The UV light source 10 is arranged in an opening at the rear of the enclosure to project its light through a similar opening in the front of the enclosure directly onto the travelling web at an angle of substantially 90° with respect to the web. The photocell detector 12 is mounted within the enclosure and arranged at an angle of approximately 45° with respect to the web so as to intercept only those visible light rays that are reflected angularly from the coating on the web. The two filters A and B are arranged within the enclosure between the web and the UV light source and between the web and the photocell detector substantially as schematically shown in FIG. 1. The photocell detector 12 is in turn connected to a recording device such as a millivolt strip chart recorder or a digital read-out millivolt meter.

In the embodiment described above the UV light source is a "Blak-Ray" long wave UV lamp Model B100 (Ultraviolet Products, Inc.). The first filter, filter A, is a UV transmitting, visible absorbing Kopp No. 40 filter which effectively reduces the output of visible light to an acceptably low level.

The second filter, filter B, comprises a combination of two Corning filters C.S. 3-74 and C.S. 5-56 which together remove any reflected UV light and reduce the sensitivity of the photocell detector 12 to normal room lighting by passing only the blue light in the visible region. Meanwhile, the fluorescent intensity is measured with a selenium photocell of high sensitivity as used in Photometer Model 200 M (Photovolt Corporation). Other liht sensing detectors such as silicon cells or photodiodes can also be used in place of the selenium photocell.

For the purpose of permitting the enclosure to scan the web, and particularly for dried coatings, to touch the web, a plurality of teflon coated rods are mounted over the front opening of the enclosure. However, it is not necessary to touch the web in order to get accurate readings. Thus, when wet coat weights are measured the UV light source enclosure is held in close proximity to but does not touch the web. This arrangement permits the coat weight measuring device of the present invention to be used at any location on the web either before, or after the coating is dried, or for a single sheet off-machine coat weight measurements. The stability of the UV light source after several hours warmup is excellent and any heat build-up in the enclosure that might effect the photocell detector's sensitivity can be eliminated with the use of a cooling fan in the enclosure. Alternatively the unit can be held at a constant temperature substantially above room temperature by controlling the cooling fan with a thermostat.

In order to demonstrate the results obtained with the technique of the present invention, the following Examples are provided:

EXAMPLE I

The optimum level of optical brightener that can be used in the present invention to yield the accuracy desired, particularly at low coat weights, is demonstrated in the following two experiments.

Hand drawdowns were made with conductive coating formulations containing 55 parts Lustra clay, 18 parts ethylated starch and 27 parts conductive resin (Dow ECR-34) containing a stilbene type optical brightener Paper White SP, C.I. No. 102, supplied by E.I. Dupont de Nemours, & Company. Two different levels of optical brightener were used, 0.1% and 1.0% by weight at 43.5% solids. Coatings were applied at 38% solids to a production grade sizepressed liquid toner basestock by wire wound rod over a coat weight range of from about 2 to 4 pounds per ream. Comparison coat weight measurements were made by the "wet weight" difference method. In this method, a preweighed sheet was coated and immediately after coating reweighed with the difference in weight corresponding to the wet weight of the coating applied. Fluorescence readings were taken of the samples using a laboratory scale mock-up of the apparatus shown in FIG. 1 which included a millivolt strip chart recorder to measure the output of the photocell.

Figure 2:
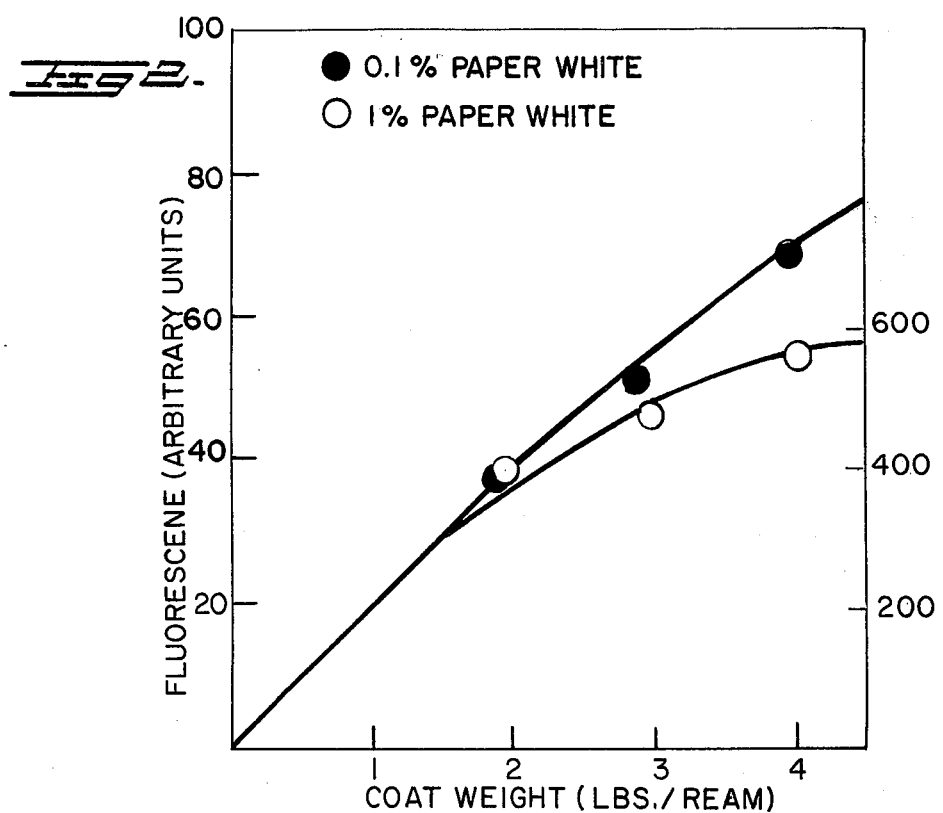
FIG. 2 is a plot of the fluoresence vs. coat weight data shown in Table I herein.

The fluorescence data obtained is recorded in Table I, and shows that at a low addition of optical brightener (0.1%), the difference between the levels of fluorescence of the uncoated and coated paper is 19.5, 18.2 and 17.9 units per pound of coating applied yielding a linear relationship over the range of from 1.9 to 3.9 pounds per ream of coating. In each case, the change in the reading obtained per pound of coating applied (column No. 4) is calculated by subtracting the initial reading (control) from the actual reading obtained and dividing that number by the coat weight applied. A plot of the data reproduced in Table I is shown in FIG. 2, with the initial reading (18 units) subtracted from the fluorescence measurements actually recorded.

TABLE I

| (1) Coat Weight (lbs/ream) | (2) Paper White (%) | (3) Fluorescence reading (Arbitrary units) | (4) Units/lb. of coating |
|---|---|---|---|
| uncoated(control) | — | 18 | 0 |
| 1.9 | 0.1 | 55 | 19.5 |
| 2.8 | 0.1 | 69 | 18.2 |
| 3.9 | 0.1 | 88 | 17.9 |
| 1.9 | 1.0 | 408 | 205 |

TABLE I-continued

| (1) Coat Weight (lbs/ream) | (2) Paper White (%) | (3) Fluorescence reading (Arbitrary units) | (4) Units/lb. of coating |
| --- | --- | --- | --- |
| 2.8 | 1.0 | 480 | 165 |
| 3.9 | 1.0 | 570 | 142 |

At the higher addition of optical brightener, the relationship becomes non-linear very quickly. The apparent fluroescence reading of 18 units on uncoated base stock results from the small level of visible light that passes through the UV transmiting/visible absorbing filter, filter A. The level of fluorescence at the 1% addition of Paper White is approximately 10 times that obtained at the 0.1% addition only at the lower coat weight range. At about 4 pounds per ream coat weight, the fluorescence difference between the 1% addition and 0.1% addition is only a factor of 8 (142/17.9). These results show that in general, increasing the amount of optical brightener in the coating reduces the range where there is a linear relationship between coat weight and fluorescence. In the non-linear region at high coat weight the accuracy of the technique is thus reduced. Therefore the amount of optical brightener added should be kept to a minimum. On the other hand, as set forth hereinbefore, the amount of optical brightener that can be added to the coating depends on the intensity of the UV lamp source, the type of optical brightener used and the sensitivity of the detecting equipment. Thus the minimum amount of optical brightener used would vary as the conditions noted above varied. It is also desirable to choose an optical brightener, and a concentration of same depending on the equipment used, that will yield readily measurable differences between the apparent fluorescence of the uncoated basestock and the level of fluorescence of the coated basestock. This latter condition produces an expanded range where the relationship between coat weight and fluorescence is linear and provides the greatest accuracy for detecting small changes in coat weights.

EXAMPLE II

Figure 3:
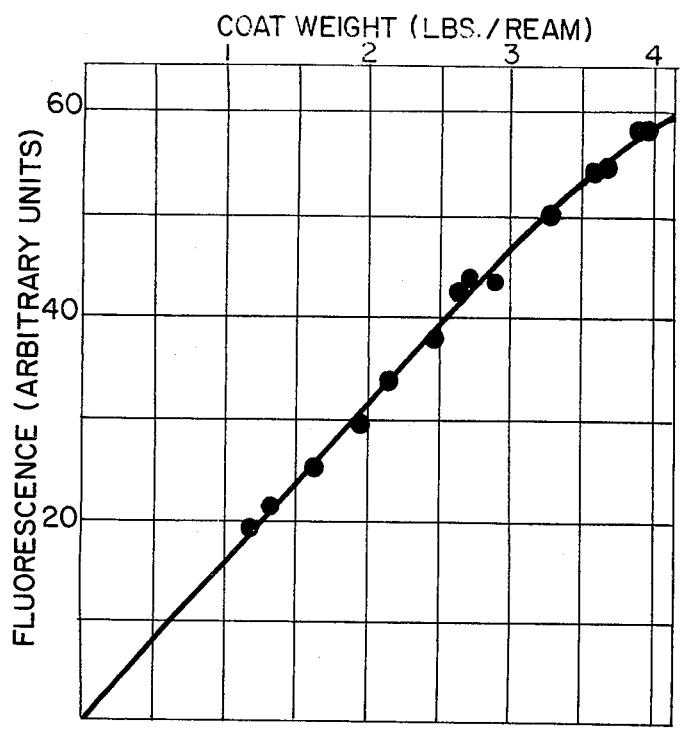
FIG. 3 is a plot of the fluorescence vs. coat weight data shown in Table II herein.

A second conductive coating formulation (60 parts Lustra clay, 20 parts Dow ECR-34 and 20 parts starch), containing Leucophor C-6902, an optical brightener of the anionic stilbene type, C.I. No. 231, manufactured by SANDOZ Colors and Chemicals, was applied to a production Electrofax liquid toner basestock in an on-machine application by a knurled roll coater. The optical brightener was added in the amount of 0.5% by weight at 36.7% solids and coat weights were varied from about 1.3 to 4.0 pounds per ream on one side of the web (C1S) by changing the speed differential between the knurled roll and the applicator roll. The fluorescence measuring equipment described hereinbefore was located after the drying oven to measure the fluorescence of the dried coating. Duplicate coat weights were also determined by ashing samples of the coated paper in order to assess the accuracy of the fluorimetric coat weight measurement method in a continuous coating operation. Coat weight and fluoescence levels are set forth in Table II where the apparent fluorescence of the uncoated basestock has been subtracted from the fluorescence readings actually obtained. The data clearly show the excellent reproduceability of the technique and the good linar relationship between the coat weight calculated, column (1) Table II, and fluorescence measured, column (2). That is, the amount of fluoresence per pound of coat weight applied only varies between 14.7 and 16.4 units in the coat weight range of from about 1.3 to 4.0 pounds per ream. Once again, as was the case in Example I, the numbers in column (3) of Table II were obtained by dividing the fluorescence readings by the coat weights calculated. The resulting plot of the data in Table II is shown in FIG. 3 where excellent linearity is demonstrated.

TABLE II

| (1) Coat Weight (lbs/ream) | (2) Fluorescence (arbitrary/units) | (3) Units/lb. of coating |
| --- | --- | --- |
| 1.28 | 21.0 | 16.4 |
| 1.40 | 22.3 | 15.9 |
| 1.70 | 26.5 | 15.6 |
| 2.0 | 31.0 | 15.5 |
| 2.2 | 35.0 | 15.9 |
| 2.5 | 39.0 | 15.6 |
| 2.7 | 43.5 | 16.1 |
| 2.8 | 44.5 | 15.9 |
| 2.9 | 44.5 | 15.3 |
| 3.3 | 50.0 | 15.2 |
| 3.6 | 54.5 | 15.1 |
| 3.7 | 55.0 | 14.7 |
| 3.9 | 58.0 | 14.9 |
| 3.95 | 59.0 | 14.9 |

EXAMPLE III

Figure 4:
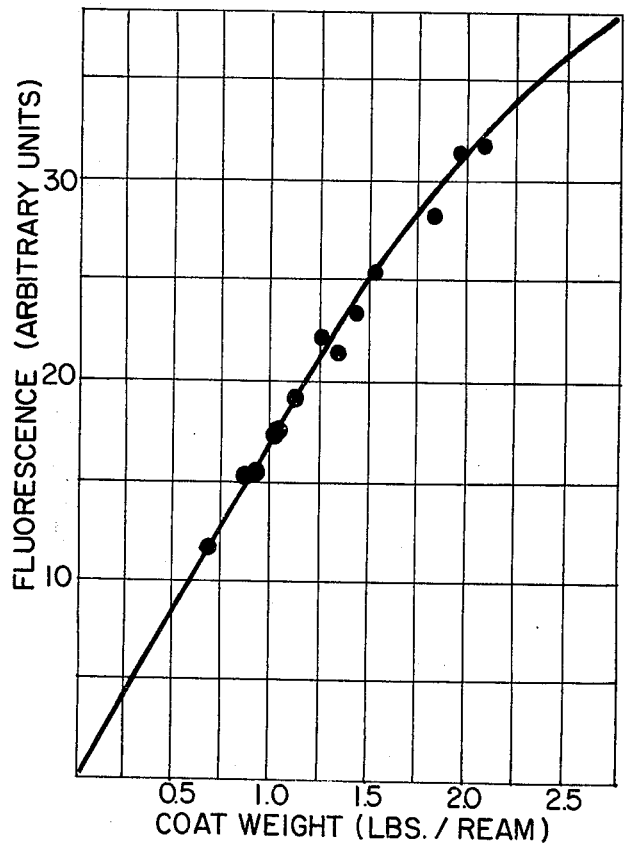
FIG. 4 is a plot of the fluorescence vs. coat weight data shown in Table III herein.

A highly pigmented coating containing 6 parts clay and 1 part starch with by weight 0.2% Paper White SP optical brightener at 43.5% solids was applied by gate roll size press on a laboratory coating apparatus over the coat weight range of from about 0.6 to 2 pounds per ream. Coat weight was varied by changing speed and pressure of the transfer rolls. The fluorescence device was located after the drying section of the coater and duplicate coat weight measurements were made by ash determination. The good linear relationship between coat weight and level of fluorescence (after subtracting the initial reading of the uncoated basestock) is shown in Table III. The data also demonstrates the excellent accuracy of the method disclosed for measuring very low coat weight. The data in Table III is plotted in FIG. 4 to show the relationship between coat weight and fluorescence.

TABLE II

| (1) Coat Weight (lbs./ream) | (2) Fluoroescence (arbitrary units) | (3) Units/lb. of coating |
| --- | --- | --- |
| 0.65 | 11.3 | 17.4 |
| 0.80 | 14.0 | 17.5 |
| 0.85 | 15.0 | 17.6 |
| 0.95 | 17.0 | 17.9 |
| 1.0 | 17.5 | 17.5 |
| 1.1 | 19.0 | 17.3 |
| 1.2 | 22.0 | 18.3 |
| 1.3 | 21.2 | 16.3 |
| 1.4 | 23.5 | 16.8 |
| 1.58 | 26.7 | 16.9 |

TABLE II-continued

| (1) Coat Weight (lbs./ream) | (2) Fluoroescence (arbitrary units) | (3) Units/lb. of coating |
| --- | --- | --- |
| 1.85 | 29.0 | 15.7 |
| 1.92 | 31.5 | 16.4 |
| 2.05 | 32.0 | 15.6 |

EXAMPLE IV

A pigmented coating containing 75% Hydragloss 90 clay (Huber Corp.), 25% alkali soluble polyethylene-acrylic acid copolymer-PCX300 (Union Carbide) and 0.1% by weight Leucophor C-6902 optical brightener at 36.7% solids was applied to 60 lb envelope base by wire wound rod. Coat weights were determined by removing the coating with hot solvent (80% toluene 20% butanol). Table IV below gives fluorescence measurement on hand sheets with coat weights ranging from 2 to 15 pounds per ream.

TABLE IV

| Coat Weight (Extracted) | Fluorescence Reading (Arbitrary Units) | Units/lb. of coating |
| --- | --- | --- |
| Uncoated | 7.5 | — |
| 2.2 | 12.5 | 2.27 |
| 4.5 | 16.8 | 2.07 |
| 4.8 | 17.8 | 2.14 |
| 5.7 | 19.2 | 2.05 |
| 9.2 | 22.3 | 1.61 |
| 11.0 | 22.9 | 1.40 |
| 11.9 | 23.9 | 1.38 |
| 14.5 | 24.5 | 1.17 |

The above table shows that a good linear relationship of fluorescent reading versus coat weight remained over the coat weight range from about 2.2 to 5.7 pounds per ream. However, at higher coat weights the level of fluorescence per lb. of coating become smaller. It can be seen that the accuracy of coat weight measurement from about 11 to 14 pounds per ream is considerably reduced presumably because of the high opacity of the pigmented coating.

EXAMPLE V

PCX300 resin (see Example IV) containing 0.04% Leucophor C-6902 optical brightener by weight to 36.7% solids was applied unpigmented by air knife at a 50 pound envelope base paper at 500 fpm. Coat weights were determined by hot solvent extraction as given in Example IV. Fluorescence measurements were made off machine on sample sheets and the data obtained is shown in Table V.

TABLE V

| Coat Weight (Extracted) | Fluorescence Reading (Arbitrary Units) | Units/lb. of coating |
| --- | --- | --- |
| Uncoated | 10.0 | — |
| 4.0 | 31.0 | 5.3 |
| 5.7 | 38.0 | 4.9 |
| 7.5 | 47.0 | 4.9 |

The data in Table V shows a good linear relationship between the fluorescence readings and the coat weights measured by hot solvent extraction over the range of from about 4 to 7.5 pounds per ream of applied coating. The targeted coat weight for the coating applied in Example V was about 5 pounds per ream. Therefore the level of addition of optical brightener used was substantially correct to give a minimum fluorescence reading between the uncoated basestock and the coated samples, and for the purpose of giving an expanded range of fluorescence readings over the desired coat weight range.

EXAMPLE VI

Paper, coated by air knife with the formulation of Example V, was sampled across the web in eight positions to determine the variation in coat weight in the cross machine direction. Fluorescence measurements were taken and Table VI shows the uniformity of the coating in the cross machine direction. Since the data from Example V demonstrated the linearity of the coat weight with fluorescence measurements, it was not necessary to make independent coat weight determinations for the data in Table VI.

TABLE VI

| Position | Fluorescent Reading (Arbitrary Units) | Coat Weight |
| --- | --- | --- |
| 1 | 37 | 5.0 |
| 2 | 36.5 | 4.9 |
| 3 | 37.0 | 5.0 |
| 4 | 37.8 | 5.15 |
| 5 | 38.0 | 5.2 |
| 6 | 36.0 | 4.8 |
| 7 | 37.3 | 5.05 |
| 8 | 37.5 | 5.1 |

Accordingly, it may be seen that the fluorimetric coat weight measurement method of the present inventon is readily adaptable to measuring the coat weight uniformity across the web. In addition, coat weight measurements in the machine direction could similarly be made either continuously on machine with a millivolt strip chart recorder or by single sheet determinations off machine. It should be appreciated that the total length of time required to make the eight readings in Table VI was about 1 minute. In contrast, conventional analytical methods such as ash content are very time consuming.

EXAMPLE VII

Another experiment was conducted to measure, for Leucophor C-6902 optical brightener, the minimum amount that could be used in a coating formulation and still yield fluorescence readings that would be useful in monitoring and measuring the coat weight of an applied coating. For this purpose, a coating formulation containing Hydrasperse clay (Huber Corporation) and PCX-300 resin (Union Carbide) in a ratio of 50/50 was made up to which was added increasing amounts of Leucophor C-6902 optical brightener. The different coatings were applied at about 6 lb/ream coat weight to a 60 pound envelope basestock by a wire wound rod. The coat weights applied were determined gravimetrically on preweighed oven dried sheets, the fluorescence of each coating was measured using the fluorimetric technique, disclosed herein and the data obtained is reproduced in Table VII.

TABLE VII

| % Optical Brightener (dry weight) | Fluorescence (Arbitrary Units) | Coat Weight (lbs./ream) |
| --- | --- | --- |
| 0 | 2.1 | 5.9 |
| .001 | 2.2 | 5.9 |
| .0021 | 2.4 | 5.9 |
| .0043 | 2.7 | 6.0 |
| .021 | 5.1 | 6.0 |
| .043 | 8.0 | 6.2 |

TABLE VII-continued

| % Optical Brightener (dry weight) | Fluorescence (Arbitrary Units) | Coat Weight (lbs./ream) |
|---|---|---|
| .21 | 18.9 | 5.9 |
| .43 | 24.0 | 5.9 |
| .86 | 27.1 | 5.9 |

The level of optical brightener addition noted in Table VII is expressed as parts of dry optical brightener per 100 parts of dry coating. Accordingly, this experiment is to be contrasted from the experiments described in Examples I–VI which employed the optical brightener in solution.

At an optical brightener level of 0.001% the fluorescence reading obtained is only 5% higher than the fluorescence reading of the coating containing no optical brightener (2.2 vs. 2.1). Thus, for the reasonable accuracy in measuring coat weights, a minimum level of optical brightener is believed to be about 0.002% which would yield an increase in fluorescence reading of 14% over the uncoated basestock. It should be understood however, that the data reproduced in Table VII and discussed here are only reliable for Leucophor C-6902 optical brightener, as used in the coating formulation described and in view of the optical system employed.

Figure 5:
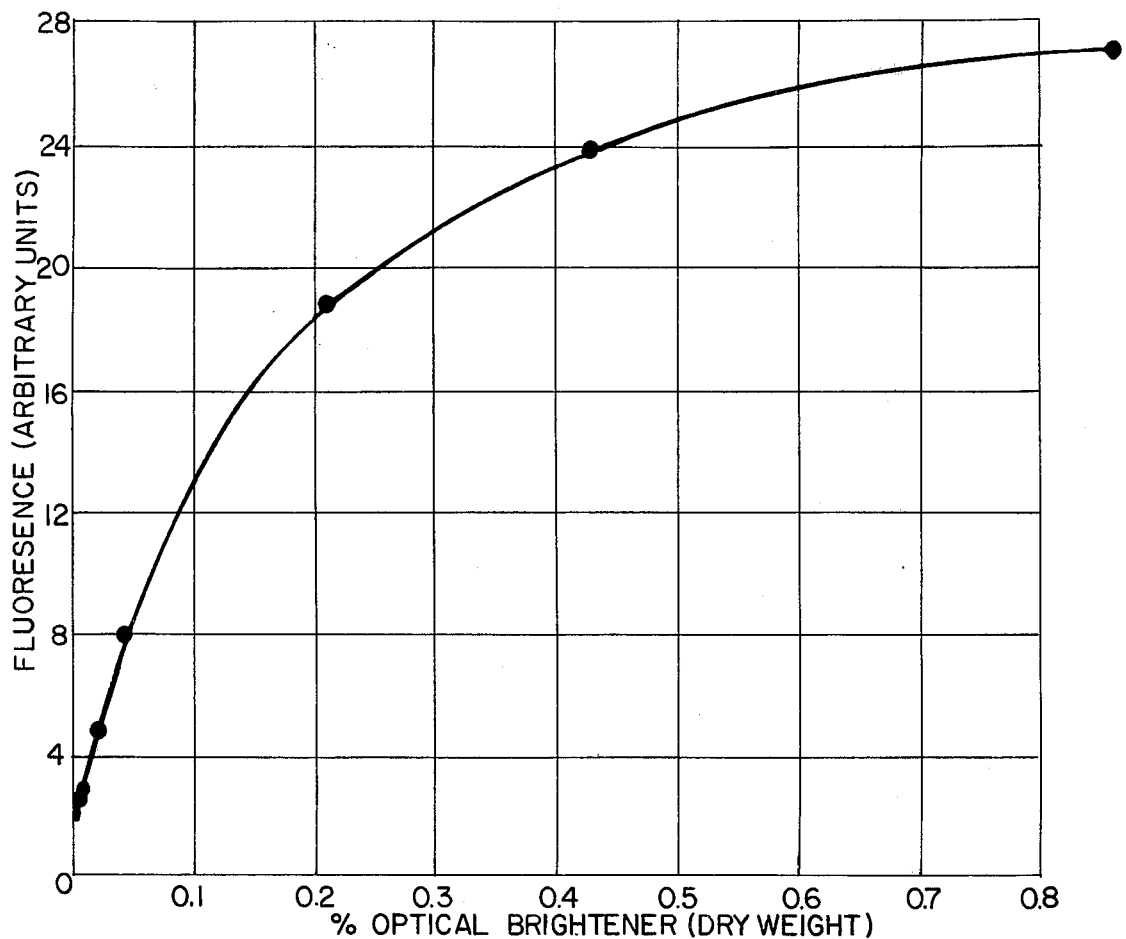
FIG. 5 is a plot of the fluorescence vs. % optical brightener data shown in Table VII herein; and, FIG. 5a is a plot of the data in FIG. 5 with the scale for % optical brightener expanded.
Figure 5A:
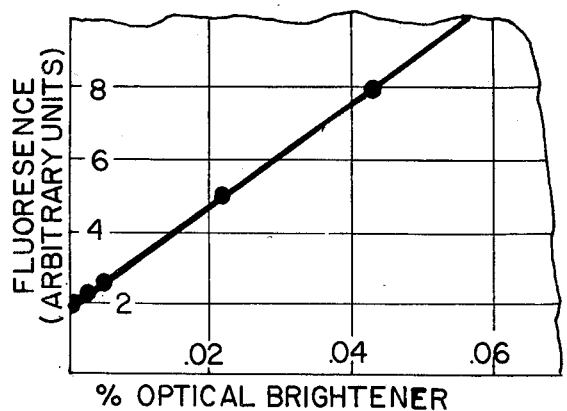

A more than adequate level of Leucophor C-6902 in the coating of Example VII was found to be about 0.86%. At this level of addition the increase in fluorescence from the 0.43% addition was only 13% or an insignificant amount to provide reliable and accurate coat weight measurements. The data included in Table VII are plotted in FIGS. 5 and 5a, and from those curves it may be seen that for accurate coat weight determination under the conditions used in generating the data in Table VII, the preferred range of addition of Leucophor C-6902 optical brightener would be from about 0.004 to 0.2% dry weight.

In each of the above Examples, no fluorescence could be detected on the non-coated sides of the C1S sheets which makes feasible the measurement of separate coat weights on each side of a C2S sheet using the technique disclosed herein. Other work with highly pigmented coatings demonstrated a reduced sensitivity of the fluorimetric technique in the coat weight range of from about 6 to 10 lbs. per ream. This result was deemed reasonable in view of the fact that with increased coat weights the UV light from the light source is not able to penetrate the coating layer as readily as at lower coat weights. Thus even though there is a greater amount of fluorescent material in a higher weight coating, no increase in fluorescence can be detected. It was also found that as the level of optical brightener was increased in the coating, the results obtained from the fluorimetric technique were linear only in the low coat weight range and became non linear at higher coat weights.

It will be understood however that the invention disclosed herein could be susceptible to modifications and changes particularly in the apparatus used in the carrying out of the method. It is therefore desired that the embodiments disclosed be considered in all respects as illustrative and not restrictive, reference being made to the appended claims rather than to the foregoing description to indicate the scope of the invention.

I claim:

1. A method of measuring the coat weight of a coating applied to a paper substrate or the like in web form comprising:
   a. adding an effective amount of a fluorescing optical brightener to the coating formulation to be applied to a substrate;
   b. applying said fluorescing optical brightener containing coating formulation to samples of said substrate at different coat weights over the coat weight range desired;
   c. scanning the coated surface of said coated samples with a UV light source;
   d. measuring the fluorescence of the coated samples;
   e. comparing the fluorescence readings obtained with the actual coat weights applied to said samples as measured by an independent method;
   f. preparing a plot of coat weight vs. fluorescence for the coatings applied; and,
   g. thereafter coating said substrate with said coating formulation and measuring the fluorescence of the coating applied for determining the coat weight applied.

2. The method of claim 1 wherein an effective amount of fluorescing optical brightener is an amount sufficient to produce a change in the fluorescence of the coated substrate as compared with the uncoated substrate of at least about 14%.

3. The method of claim 1 wherein the addition of fluorescing optical brightener to the coating formulation is at least about 0.002% by dry weight.

4. The method of claim 1 wherein the addition of fluorescing optical brightener to the coating formulation is from about 0.004% to about 0.2% dry weight.

5. The method of claim 1 wherein the plot of coat weight vs. fluorescence is substantially linear over the coat weight range of from about 0 to 5 pounds per ream of applied coating.

6. The method of claim 1 wherein the coating formulation is applied to each side of said substrate and the fluorescence of each side of said substrate is measured for determining the coat weights applied.

7. The method of claim 1 wherein the fluorescing optical brightener fluoresces in the range of from about 400 to 500 nanometers.

8. The method of claim 1 wherein the fluorescing optical brightener is selected from the class known as stilbene type optical brighteners.

9. The method of claim 1 wherein the substrate is coated on a coating machine in a continuous coating application and the fluorescence of the coating applied to said substrate is continuously monitored and measured on said machine for determining the coat weight appled.

* * * * *